United States Patent
Langberg et al.

(10) Patent No.: US 6,810,882 B2
(45) Date of Patent: Nov. 2, 2004

(54) TRANSLUMINAL MITRAL ANNULOPLASTY

(75) Inventors: Jonathan J. Langberg, Atlanta, GA (US); Michael D. Lesh, Mill Valley, CA (US); Erik van der Burg, Sunnyvale, CA (US)

(73) Assignee: ev3 Santa Rosa, Inc., Plymouth, MN (US)

( * ) Notice: Subject to any disclaimer, the term of this patent is extended or adjusted under 35 U.S.C. 154(b) by 0 days.

(21) Appl. No.: 09/909,101

(22) Filed: Jul. 19, 2001

(65) Prior Publication Data

US 2002/0103532 A1 Aug. 1, 2002

Related U.S. Application Data

(63) Continuation of application No. 09/774,869, filed on Jan. 30, 2001, now Pat. No. 6,537,314.

(51) Int. Cl.⁷ .............................................. A61B 19/00
(52) U.S. Cl. ...................................... 128/898; 623/2.37
(58) Field of Search ................................. 623/1.1, 1.11, 623/1.15, 1.24, 1.26, 2.1, 2.11, 2.37, 900, 904; 606/139, 108; 600/37; 128/898

(56) References Cited

U.S. PATENT DOCUMENTS

| | | | |
|---|---|---|---|
| 4,128,100 | A | 12/1978 | Wendorff |
| 4,917,698 | A | 4/1990 | Carpentier et al. |
| 5,006,106 | A | 4/1991 | Angelchik |

(List continued on next page.)

FOREIGN PATENT DOCUMENTS

| | | |
|---|---|---|
| DE | 196 05 042 A1 | 1/1998 |
| EP | 0 727 239 A2 | 8/1996 |
| EP | 0727 239 A3 | 4/1997 |
| WO | WO 91/19465 | 12/1991 |
| WO | WO 96/34211 | 10/1996 |
| WO | WO 98/29041 | 7/1998 |
| WO | WO 96/34211 | 10/1998 |
| WO | WO 99/30647 | 6/1999 |
| WO | WO 99/44534 | 9/1999 |
| WO | WO 00/06026 | 2/2000 |
| WO | WO 00/06027 | 2/2000 |
| WO | WO 00/06028 | 2/2000 |
| WO | WO 00/16700 | 3/2000 |
| WO | WO 00/18320 | 4/2000 |
| WO | WO 01/00111 A1 | 1/2001 |
| WO | WO 01/00114 A1 | 1/2001 |
| WO | WO 01/28455 A1 | 4/2001 |

OTHER PUBLICATIONS

U.S. patent application Ser. No. 60/348,424, Taylor et al., filed Jan. 2002.
U.S. patent application Ser. No. 60/279,973, Taylor et al., filed Mar. 2001.
U.S. patent application Ser. No. 60/278,153, Cohn et al., filed Mar. 2001.
U.S. patent application Ser. No. 60/339,481, Cohn et al., filed Oct. 2001.
U.S. patent application Ser. No. 60/312,217, Taylor et al., filed Aug. 2001.

(List continued on next page.)

*Primary Examiner*—David J. Isabella
*Assistant Examiner*—Urmi Chattopadhyay
(74) *Attorney, Agent, or Firm*—Knobbe, Martens, Olson & Bear, LLP

(57) ABSTRACT

A mitral annuloplasty and left ventricle restriction device is designed to be transvenously advanced and deployed within the coronary sinus and in some embodiments other coronary veins. The device places tension on adjacent structures, reducing the diameter and/or limiting expansion of the mitral annulus and/or limiting diastolic expansion of the left ventricle. These effects may be beneficial for patients with dilated cardiomyopathy.

65 Claims, 13 Drawing Sheets

U.S. PATENT DOCUMENTS

| | | |
|---|---|---|
| 5,041,130 A | 8/1991 | Cosgrove et al. |
| 5,061,277 A | 10/1991 | Carpentier et al. |
| 5,064,431 A | 11/1991 | Gilbertson et al. |
| 5,099,838 A | 3/1992 | Bardy |
| 5,104,407 A | 4/1992 | Lam et al. |
| 5,163,955 A | 11/1992 | Love et al. |
| 5,165,403 A | 11/1992 | Mehra |
| 5,201,880 A | 4/1993 | Wright et al. |
| 5,290,300 A | 3/1994 | Cosgrove et al. |
| 5,350,420 A | 9/1994 | Cosgrove et al. |
| 5,450,860 A | 9/1995 | O'Connor |
| 5,476,471 A | 12/1995 | Shifrin et al. |
| 5,545,209 A | 8/1996 | Roberts et al. |
| 5,562,619 A | 10/1996 | Mirarchi et al. |
| 5,593,424 A | 1/1997 | Northrup III |
| 5,702,343 A | 12/1997 | Alferness |
| 5,716,397 A | 2/1998 | Myers |
| 5,824,066 A | 10/1998 | Gross |
| 5,891,108 A | 4/1999 | Leone et al. |
| 5,919,233 A | 7/1999 | Knopf et al. |
| 5,935,081 A * | 8/1999 | Kadhiresan ............... 600/513 |
| 5,961,440 A | 10/1999 | Schweich, Jr. et al. |
| 5,961,545 A | 10/1999 | Lentz et al. |
| 6,001,127 A | 12/1999 | Schoon et al. |
| 6,019,739 A * | 2/2000 | Rhee et al. ............... 606/148 |
| 6,045,497 A | 4/2000 | Schweich, Jr. et al. |
| 6,050,936 A | 4/2000 | Schweich, Jr. et al. |
| 6,051,020 A | 4/2000 | Goicoechea et al. |
| 6,059,715 A | 5/2000 | Schweich, Jr. et al. |
| 6,077,214 A | 6/2000 | Mortier et al. |
| 6,077,296 A | 6/2000 | Shokoohi et al. |
| 6,095,968 A | 8/2000 | Snyders |
| 6,110,100 A | 8/2000 | Talpade |
| 6,123,662 A | 9/2000 | Alferness et al. |
| 6,143,024 A | 11/2000 | Campbell et al. |
| 6,146,325 A | 11/2000 | Lewis et al. |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,122 A | 12/2000 | Alferness |
| 6,171,329 B1 | 1/2001 | Shaw et al. |
| 6,174,279 B1 | 1/2001 | Girard |
| 6,183,411 B1 | 2/2001 | Mortier et al. |
| 6,183,512 B1 | 2/2001 | Howanec, Jr. et al. |
| 6,193,648 B1 | 2/2001 | Krueger |
| 6,210,432 B1 | 4/2001 | Solem et al. |
| 6,217,610 B1 | 4/2001 | Carpentier et al. |
| 6,221,103 B1 | 4/2001 | Melvin |
| 6,230,714 B1 | 5/2001 | Alferness et al. |
| 6,241,654 B1 | 6/2001 | Alferness |
| 6,250,308 B1 | 6/2001 | Cox |
| 6,260,552 B1 | 7/2001 | Mortier et al. |
| 6,261,222 B1 | 7/2001 | Mortier et al. |
| 6,264,602 B1 | 7/2001 | Mortier et al. |
| 6,402,781 B1 | 6/2002 | Langberg et al. |
| 6,569,198 B1 * | 5/2003 | Wilson et al. ............ 623/2.37 |
| 2002/0183835 A1 * | 12/2002 | Taylor et al. ............ 623/2.11 |
| 2002/0183836 A1 * | 12/2002 | Liddicoat et al. ......... 623/2.11 |
| 2002/0183837 A1 * | 12/2002 | Streeter et al. ........... 623/2.11 |
| 2002/0183838 A1 * | 12/2002 | Liddicoat et al. ......... 623/2.11 |
| 2002/0183841 A1 * | 12/2002 | Cohn et al. .............. 623/2.36 |

OTHER PUBLICATIONS

U.S. patent application Ser. No. 60/283,820, Cohn et al., filed Apr. 2001.

U.S. patent application Ser. No. 60/280,038, Cohn et al., filed Mar. 2001.

U.S. patent application Ser. No. 60/279,974, Taylor et al., filed Mar. 2001.

U.S. patent application Ser. No. 60/242,466, Streeter, filed Oct. 2000.

U.S. patent application Ser. No. 60/266,766, Cohn et al., filed Feb. 2001.

U.S. patent application Ser. No. 60/213,782, Cohn et al., filed Jun. 2000.

U.S. patent application Ser. No. 60/273,893, Cohn et al., filed Mar. 2001.

Boyd et al., *Tricuspid annuloplasty*, Sep. 1974, The Journal of Thoracic and Cardiovascular Surgery, p. 344,351.

Kurlansky et al., *Adjustable Annuloplasty for Tricuspid Insufficiency*, Oct. 1987, The Annals of Thoracic Surgery, p. 404–406.

Alonso–Lej, *Adjustable Annuloplasty for Tricuspid Insufficiency*, Sep. 1988, The Annals of Thoracic Surgery, Letter to the Editor, p. 368–369.

Chachques et al., *Latissimus Dorsi Dynamic Cardiomyoplasty*, 1989, The Society of Thoracic Surgeions, p. 600–604.

McCarthy et al., *Clinical experience with the Novacor ventricular assist system*, May 1990, J Thorac Cardiovasc Surg, p. 578–587.

Farrar et al., *A New Skeletal Muscle Linear–pull Energy Converter as a Power Source for Prosthetic Circulatory Support Devices*, Sep. 1992, The Journal of Heart and Lung Transplantation, p. S341–S349.

Bolling et al., *Early outcome of mitral valve reconstruction in patients with end–stage cardiomyopathy*, Apr. 1995, The Journal of Thoracic and Cardiovascular Surgery, p. 676–683.

Bach et al., *Early improvement in congestive heart failure after correction of secondary mitral regurgitation in end–stage cardiomyopathy*, Jun. 1995, American Heart Journal, p. 1165–1170.

Bearnson et al., *Development of a Prototype Magneticallly Suspended Rotar Ventricular Assist Device*, ASAIO Journal 1996, p. 275–280.

*Thoratec Ventricular Assist Device System*, 1996 Brochure.

McCarthy et al., *Early Results with Partial Left VEntriculectomy*, May 1997, Presented at the 77th Annual Meeting of the American Association of thoracic Surgeons.

Buchanan et al., *Circumferential Suture of the Mitral Annulus for Correction of Mitral Regurgitation in Dogs*, 1998, Veterinary Surgery vol. 27, p. 182–193.

Yamani et al., *Surgical Treatment of Chronic Heart Failure*, 2000, Congestive Heart Failure Second Edition, p. 767–784.

Bristow et al., *Heart Failure Management Using Implantable Devices for Ventricular Resynchronization: Comparison of Medical Therapy, Pacing and Defibrillation in Chronic Heart Failure (COMPANION) Trial*, Sep. 2000, Journal of Cardiac Failure, vol. 6, No. 3, p. 276–285.

Smolens et al., *Mitral Valve Repair in Heart Failure*, 2000, European Journal of Heart Failure 2, p. 365–371.

* cited by examiner

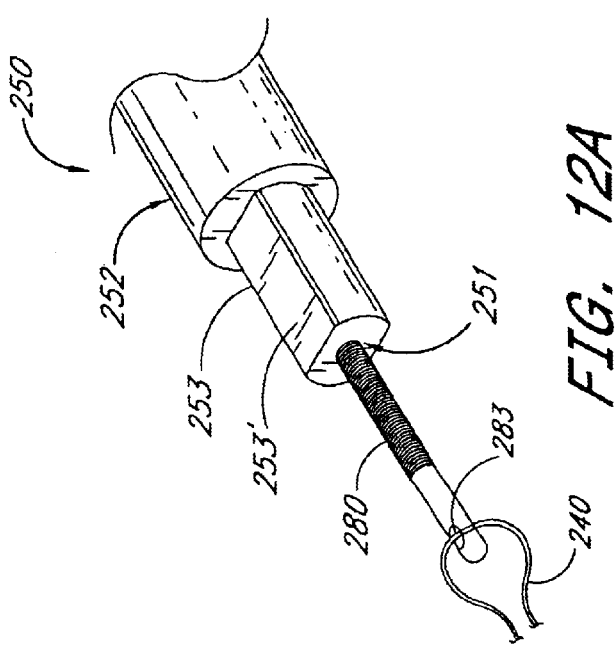
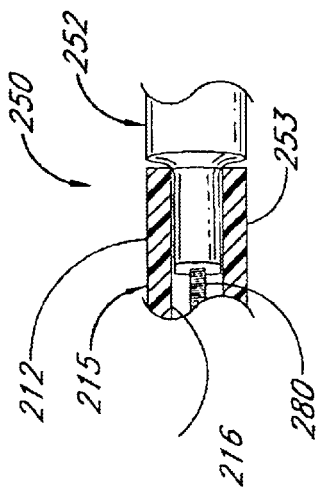
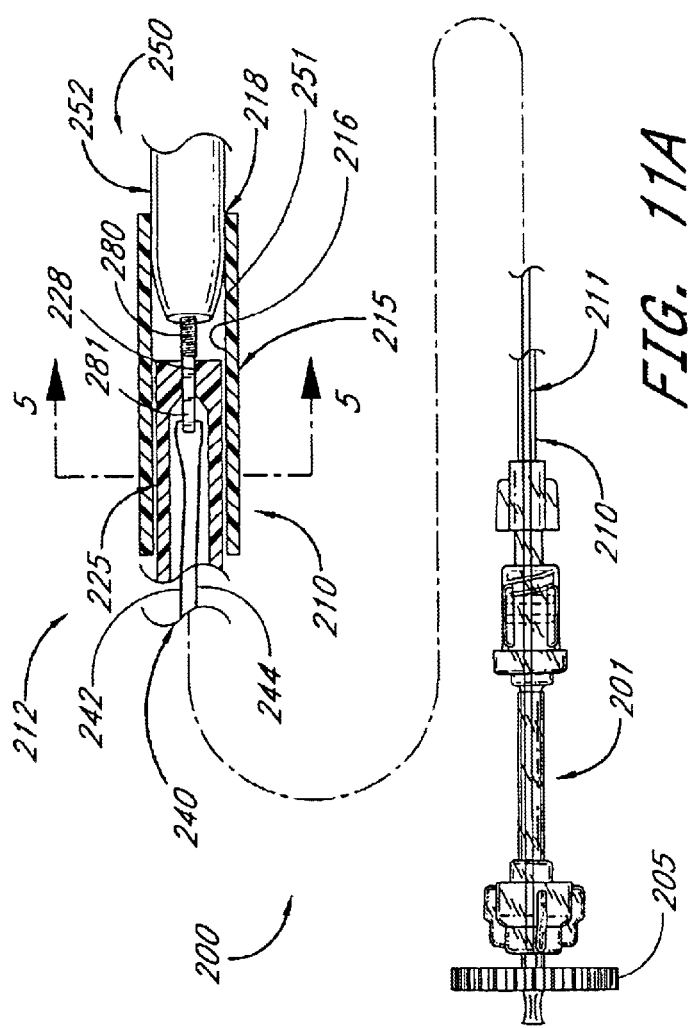
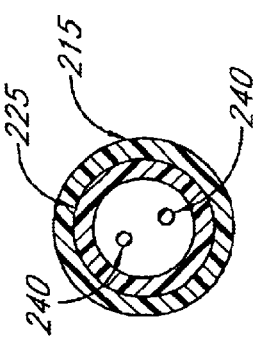

TRANSLUMINAL MITRAL ANNULOPLASTY

This application is a continuation of U.S. application Ser. No. 09/774,869 filed on Jan. 30, 2001, now U.S. Pat. No. 6,537,314, entitled Percutaneous Mitral Annuloplasty and Cardiac Reinforcement.

The present invention relates to intravascular prostheses for remodeling an extravascular anatomical structure. In one application, the present invention relates to a mitral annuloplasty and cardiac reinforcement device which is transluminally implantable in the coronary sinus.

BACKGROUND OF THE INVENTION

Dilated cardiomyopathy occurs as a consequence of many different disease processes that impair myocardial function, such as coronary artery disease and hypertension. The left ventricle enlarges and the ejection fraction is reduced. The resulting increase in pulmonary venous pressure and reduction in cardiac output cause congestive heart failure. Enlargement of the mitral annulus and left ventricular cavity produce mitral valvular insufficiency. This in turn, causes volume overload that exacerbates the myopathy, leading to a vicious cycle of progressive enlargement and worsening mitral regurgitation.

According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques have been developed to repair a diseased or damaged valve. One repair technique which has been shown to be effective in treating incompetence, particularly of the mitral and tricuspid valves, is annuloplasty, in which the effective size of the valve annulus is contracted by attaching a prosthetic annuloplasty ring to the endocardial surface of the heart around the valve annulus. The annuloplasty ring comprises an inner substrate of a metal such as stainless steel or titanium, or a flexible material such as silicone rubber or Dacron cordage, covered with a biocompatible fabric or cloth to allow the ring to be sutured to the heart tissue. The annuloplasty ring may be stiff or flexible, may be split or continuous, and may have a variety of shapes, including circular, D-shaped, C-shaped, or kidney-shaped. Examples are seen in U.S. Pat. Nos. 4,917,698, 5,061,277, 5,290,300, 5,350,420, 5,104,407, 5,064,431, 5,201,880, and 5,041,130, which are incorporated herein by reference.

Annuloplasty rings may also be utilized in combination with other repair techniques such as resection, in which a portion of a valve leaflet is excised, the remaining portions of the leaflet are sewn back together, and a prosthetic annuloplasty ring is then attached to the valve annulus to maintain the contracted size of the valve. Other valve repair techniques in current use include commissurotomy (cutting the valve commissures to separate fused valve leaflets), shortening mitral or tricuspid valve chordae tendonae, reattachment of severed mitral or tricuspid valve chordae tendonae or papillary muscle tissue, and decalcification of the valve leaflets or annulus. Annuloplasty rings may be used in conjunction with any repair procedures where contracting or stabilizing the valve annulus might be desirable.

Although mitral valve repair and replacement can successfully treat many patients with mitral valvular insufficiency, techniques currently in use are attended by significant morbidity and mortality. Most valve repair and replacement procedures require a thoracotomy, usually in the form of a median sternotomy, to gain access into the patient's thoracic cavity. A saw or other cutting instrument is used to cut the sternum longitudinally, allowing the two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta to occlude the aortic lumen between the brachiocephalic artery and the coronary ostia. Cardioplegic fluid is then injected into the coronary arteries, either directly into the coronary ostia or through a puncture in the ascending aorta, to arrest cardiac function. The patient is placed on extracorporeal cardiopulmonary bypass to maintain peripheral circulation of oxygenated blood.

Of particular interest in the present application are techniques for the repair and replacement of the mitral valve. The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into an anterior position. An opening, or atriotomy, is then made in the right side of the left atrium, anterior to the right pulmonary veins. The atriotomy is retracted by means of sutures or a retraction device, exposing the mitral valve adjacent to the atriotomy. One of the previously identified techniques may then be used to repair or replace the valve.

An alternative technique for mitral valve access has been used when a median sternotomy and/or rotational manipulation of the heart are inappropriate. In this technique, a thoracotomy is made in the right lateral side of the chest, usually in the region of the fourth or fifth intercostal space. One or more ribs may be removed from the patient, and other ribs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for cannulation of the aorta and/or coronary arteries to induce cardioplegia, manipulation of surgical instruments, removal of excised tissue, and introduction of an annuloplasty ring or a replacement valve through the atriotomy for attachment within the heart.

Mitral valve surgery, including mitral annuloplasty, is usually applied to patients with intrinsic disease of the mitral apparatus. As described above, these patients may have scarring, retraction, tears or fusion of valve leaflets as well as disorders of the subvalvular apparatus. Definitive repair requires direct visualization of the valve.

Patients who develop mitral regurgitation as a result of dilated cardiomyopathy do not have intrinsic mitral valve disease. Regurgitation occurs as the result of the leaflets being moved back from each other by the dilated annulus. The ventricle enlarges and becomes spherical, pulling the papillary muscles and chordae away from the plane of the valve and further enlarging the regurgitant orifice. In these patients, correction of the regurgitation does not require repair of the valve leaflets themselves, but simply a reduction in the size of the annulus and the sphericity of the left ventricle.

Mitral annuloplasty without repair of the leaflets or chordae has been shown to be effective in patients with dilated cardiomyopathy who are refractory to conventional medical therapy. Bolling and coworkers have operated on a cohort of such patients with New York Heart Association Class III and IV symptoms. Average symptom severity decreased from 3.9 preoperatively to 2.0 after surgery. Hemodynamics and ejection fraction improved significantly. Other investigators have achieved similar results as well. However, the morbidity, risks and expense of surgical annuloplasty are very high in patients with cardiomyopathy and congestive heart failure. Thus, a variety of new techniques for the treatment of congestive heart failure are being explored as adjuncts to drug therapy.

Several cardiac restraint devices have been described. U.S. Pat. No. 5,702,343 to Alferness discloses a cardiac reinforcement device that is applied as a jacket over the epicardium in order to limit diastolic expansion. However, this requires an open chest operation to implant and does not directly affect the diameter of the mitral annulus. Another approach is disclosed in U.S. Pat. No. 5,961,440 to Schweich, et al., in which tension members are placed through opposite walls of the heart such that they span the ventricle. Less invasive and "minimally" invasive techniques for valve repair and replacement continue to evolve, both on a stopped heart and on a beating heart. These techniques may provide some benefits over open chest procedures, but they are still attended by significant morbidity and mortality risks.

A need therefore remains for methods and devices for treating mitral valvular insufficiency, which are attended by significantly lower morbidity and mortality rates than are the current techniques, and therefore would be well suited to treat patients with dilated cardiomyopathy. Optimally, the procedure can be accomplished through a percutaneous, transluminal approach, using simple, implantable devices which do not depend upon prosthetic valve leaflets or other moving parts.

SUMMARY OF THE INVENTION

There is provided in accordance with one aspect of the present invention, a method of performing transluminal mitral annuloplasty. The method comprises the steps of providing a catheter, having a prosthesis thereon. The catheter is inserted into the venous system, and the prosthesis is transluminally advanced into the coronary sinus. A component on the prosthesis is rotated to cause the prosthesis to exert a compressive force on the adjacent atrial musculature.

The method may further comprise the step of percutaneously accessing the venous system prior to the transluminally advancing step. The access may be accomplished through one of the internal jugular, subclavian or femoral veins.

The method may further comprise the steps of first measuring the coronary sinus, and then selecting an appropriately sized prosthesis prior to the inserting step. Hemodynamic function may be measured following the rotating step. The method may additionally comprise the step of determining an ongoing drug therapy, taking into account the post implantation hemodynamic function.

In accordance with another aspect of the present invention, there is provided a method of providing a therapeutic compressive force against a tissue structure which is adjacent to a vessel wall. The method comprises the steps of positioning a device in the vessel, and rotating at least a part of a forming element within the device to cause the device to exert a force against the wall of the vessel thereby exerting a force against the adjacent tissue structure. The device is thereafter deployed within the vessel. Preferably, the positioning step is accomplished percutaneously. In one application, the tissue structure comprises the mitral valve annulus. Alternatively, the tissue structure comprises the left ventricle.

In accordance with a further aspect of the present invention, there is provided a method of performing annuloplasty of the mitral valve. The method comprises positioning a prosthesis in the coronary sinus. A first portion of the device is rotated with respect to a second portion of the device, to cause the device to bend into an arcuate configuration, to provide a compressive force on the mitral valve annulus. The device is thereafter secured in the arcuate configuration within the coronary sinus.

Preferably, the method additionally comprises the step of percutaneously accessing the venous system prior to the positioning step. The securing step may comprise engaging a first threaded surface with a second threaded surface. Alternatively, the securing step may comprise providing an interference fit, an adhesive bond, a knot or a compression fit.

In one application of the invention, the method additionally comprises the step of measuring the coronary sinus and then selecting an appropriately sized prosthesis prior to the positioning step. The method may additionally comprise the step of measuring hemodynamic function following the rotating step. An ongoing drug therapy may be determined, taking into account the post implantation hemodynamic function.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 11A is a segmented view of the device assembly shown in FIG. 10, and shows a partially exploded view of a region of the assembly.

FIG. 11B shows a transverse cross-sectional view taken along 11B—11B in FIG. 11A.

FIG. 12A shows an exploded perspective view of one region of another device assembly according to the invention.

FIG. 12B shows a partially cross-sectioned side view of a region of a device assembly similar to that shown in FIG. 12.

DETAILED DESCRIPTION OF PREFERRED EMBODIMENTS

The present invention provides a method and apparatus for performing mitral annuloplasty and remodeling of the left ventricle using a device that may be introduced percutaneously, and placed within the coronary venous system of the heart. The device exerts compressive force on the mitral annulus and left ventricle, reducing the severity of mitral regurgitation and the size of the left ventricular cavity. The device thus enables reduction of the mitral annulus and constraint of the diastolic expansion of the left ventricle yet without the morbidity and other risks associated with open chest surgery.

The present inventors have determined that the coronary sinus and veins provide an ideal conduit for the positioning of an intravascular prosthesis for remodeling the mitral annulus, since they are positioned adjacent the mitral annulus and interventricular septum. The coronary sinus is contained within the atrioventricular groove, and is in close proximity to the posterior, lateral and anterior aspects of the mitral annulus. The coronary sinus and coronary veins are cannulated currently during any of a variety of percutaneous transvenous diagnostic and therapeutic procedures. Permanent placement of pacemaker and defibrillator leads within the coronary sinus and veins is both safe and well tolerated.

The annuloplasty system consists of several components. There is a delivery system intended to be introduced percutaneously into a central vein such as the internal jugular, subclavian or femoral veins and to cannulate the coronary sinus. The implant of the present invention is deployed from the delivery catheter into the coronary venous system. Additional tools may be placed through or along the delivery catheter to position the device, apply elements in place, and to control and/or cut the tensioning elements from the delivery system as will be discussed.

Figure 1:
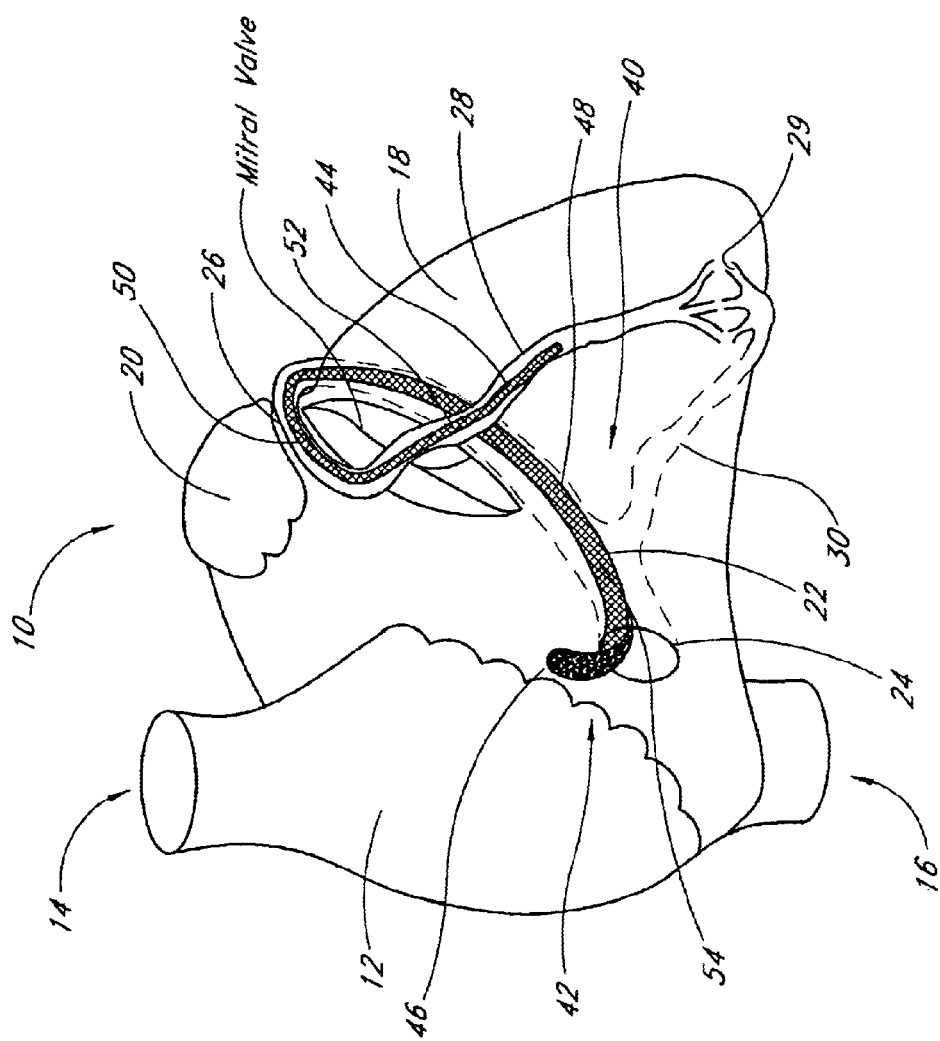
FIG. 1 is a schematic illustration of the heart, showing one embodiment of the mitral annuloplasty device of the present invention deployed within the coronary venous system.

Referring to FIG. 1, there is illustrated a schematic view of the heart 10, having a mitral annuloplasty and cardiac reinforcement device 40 positioned therein. The heart 10 generally comprises a right atrium 12, in communication with the superior vena cava 14 and inferior vena cava 16. The left ventricle 18 is positioned below the left atrial appendage 20. Relevant portions of the coronary vasculature include the coronary sinus 22, which extends from the ostium 24 to the junction 26 of the coronary sinus and the great cardiac vein 28. There may be anastomotic connections 29 between the great cardiac vein 28 and the middle cardiac vein 30, as is well understood in the art.

One embodiment of a mitral annuloplasty and cardiac reinforcement device 40 in accordance with the present invention is illustrated generally in the coronary sinus 22. In particular, the device 40 extends from a proximal end 42 to a distal end 44. The proximal end 42 lies against the posterior aspect of the interatrial septum 46. The midportion 48 of the device 40 is positioned within the coronary sinus 22. The transitional section 50 of the device 40 lies at the junction 26 of the coronary sinus 22 and the great cardiac vein 28. The distal end 44 of the device 40 is lodged in the great cardiac vein 28.

The transitional region 50 is designed to reside in the proximal portion of the great cardiac vein 28. By deflecting out of the plane of the coronary sinus 22, it serves as an anchor 52 and prevents the device 40 from slipping out of the coronary sinus 22 when tension is applied. This embodiment of an anchor 52 is very flaccid and flexible, thereby minimizing the risk of erosion of the device 40 through the wall of the great cardiac vein or other aspect of the coronary venous system. The proximal end 42 of the device 40 lies outside the ostium 24 of the coronary sinus 22 and is curved upward so as to anchor against the posterior aspect of the interatrial septum 46. The proximal end 42 is semicircular in shape and elliptical in profile so that no edges will promote erosion of adjacent tissue.

As an alternative anchor 52 to the distal extension of the device 40, any of a variety of structures may be provided. In general, the deployed device 40 will contact the wall of the coronary sinus 22 along the inside radius of its arcuate path. Thus, a tissue contacting surface 54 on the concave side of the deployed device 40 may be provided with any of a variety of friction enhancing surface structures, such as a plurality of transverse ridges, teeth or other projections, or modified surface textures to enhance friction. Alternatively, tissue engaging or piercing structures such as barbs may be provided on the surface 54 to engage the wall of the coronary sinus 22 to resist movement of the device 40.

While use of such structures as anchors may provide some benefit in certain applications, embodiments herein shown and described are believed to be particularly useful in one aspect specifically because they operate without the need for such aggressive tissue engagement. It is apparent to one of ordinary skill based upon this disclosure that the present embodiments provide independent device manipulation and shape control that allow for sufficient forces to be applied to the mitral valve without requiring the possibly harmful effects of puncturing and grabbing tissue within the sinus for the remodeling process. In one regard, the independent action of a barbless design allows for adjustment in both the tightening and loosening directions with reduced risk of significant tissue damage or erosion. In another regard, the present device according at least to certain embodiments beneficially maintains its length throughout its modified range of shapes while the sinus and adjacent valve annulus reduce their dimensions under the force of remodeling. In still a further regard, the independent action and lack of tissue piercing and grabbing anchors allow for the device to be removed from the patient after initial implantation within the sinus, such as for example in the event of complications or in applications intended to be temporary remedial measures, such as for bridging a patient. Further to this regard, various shapes and sizes of devices may be required in a given patient before the appropriate one is found according to the observed in vivo response to implantation.

The specific dimensions, construction details and materials for the mitral annuloplasty and cardiac reinforcement device 40 can be varied widely, as will be appreciated by those of skill in the art in view of the disclosure herein. For example, dimensional adjustments may be made to accommodate different anatomical sizes and configurations. Materials and construction details can be varied to accommodate different tensioning mechanisms and other considerations.

Figure 2:
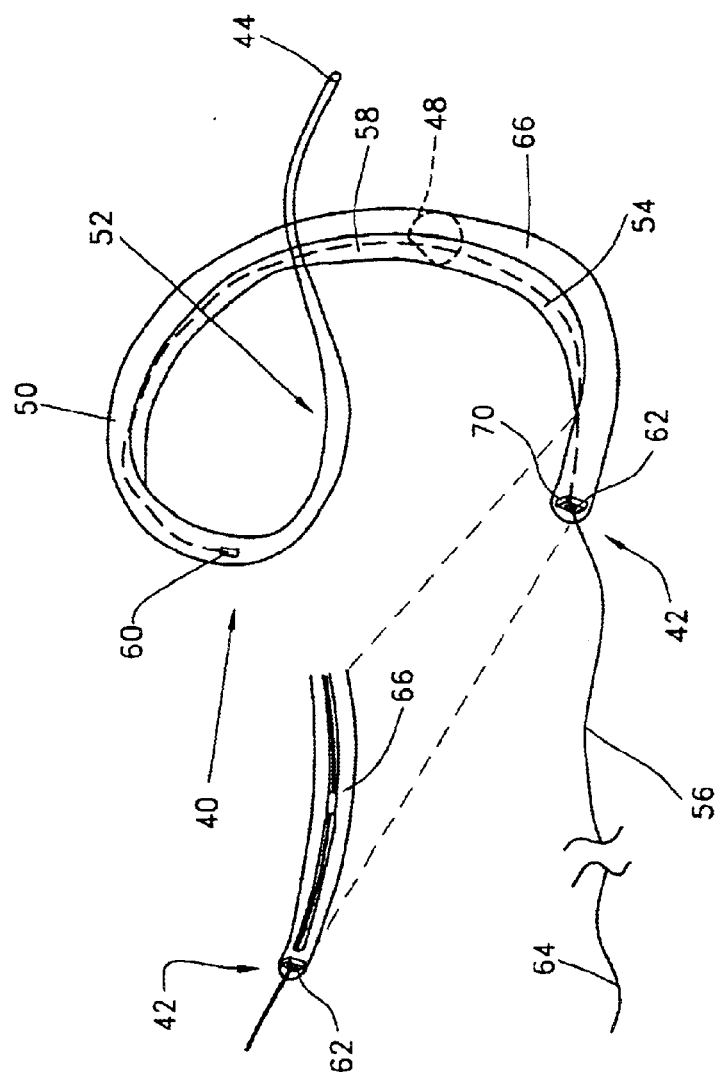
FIG. 2 is a schematic illustration of the mitral annuloplasty device shown in FIG. 1.

In general, the device 40 has an overall length from proximal end 42 to distal end 44 within the range of from about 2 cm to about 10 cm, in an embodiment such as that illustrated in FIG. 2 in which the anchor 52 comprises a distal extension of the body 66 for lodging within the great cardiac vein 28. One embodiment of the device 40 includes an elongate flexible body 66 about eight centimeters in length. In this embodiment, the body 66 is preferably elliptical in cross section so that it will bend in the plane of the coronary sinus 22 and mitral annulus when force is applied to the tensioning element within it (discussed below). Distally the device tapers and transitions to a round cross-section.

Referring to FIG. 2, there is illustrated an embodiment of the device 40 having a forming element 56 therein. Manipulation of the forming element 56 allows the device to be moved from a flexible orientation to enable percutaneous insertion into the vascular system and navigation into the coronary sinus, to an arcuate configuration for compressing at least a portion of the mitral annulus. The device 40 may be advanced from the first, flexible configuration to the second, arcuate configuration by either axial proximal retraction or distal advancement of the forming element 56 with respect to the body 66, depending upon the particular design.

In general, the device 40 comprises an elongate flexible support 58, extending from a proximal end 42 at least as far as a point of attachment 60. The support 58 may be a portion of the body 66 or may be a distinct component as will be discussed. The support 58 has a fixed length, and is relatively axially noncompressible or expandable. Thus, proximal retraction of the forming element 56 compared to the proximal end of the support 58 will cause the support 58 to deflect in a first direction. Distal axial advancement of the forming element 56 with respect to the support 58 will cause lateral deflection of the support 58 in a second direction. This basic steering configuration can be embodied in many forms, which can be optimized by those of skill in the art to suit a particular construction for the body 66 depending upon the desired dimensions and clinical performance.

The forming element 56 extends from the proximal end 42 through the device 40 to the point of attachment 60. At the point of attachment 60, the forming element 56 is mechanically linked, and preferably, directly linked to the support 58. A proximal extension 64 of the forming element 56 extends from the proximal end 42 of the device 40, such as through an aperture 62. Proximal retraction of the forming element 56 through the aperture 62 causes the device 40 to bend from an implantation orientation for navigating the coronary vasculature during implantation to a formed orientation for compression and constraint of the coronary sinus 22 and adjacent structures.

In the formed orientation, the device 40 preferably provides a compressive force against the mitral annulus as has been discussed. This is accomplished by forming the device into an arcuate configuration. Generally, the best fit curve of constant radius to which the formed device conforms has a radius within the range of from about 1.0 cm to about 2.0 cm.

The forming element may comprise any of a variety of components, such as a polymeric or metal wire or strand, a multifillament braided or woven line, a metal or polymeric ribbon, or other structure capable of retaining the device 40 under tension in the coronary sinus 22.

The device 40 further comprises a support 58, which may be the body 66 of the device 40 or a separate element positioned therein. In an embodiment in which the support 58 is a separate element contained within the device 40, support 58 may comprise any of a variety of generally axially non-compressible elements such as a metal or polymeric wire or column, ribbon, or "bottomed out" spring which facilitates lateral bending but inhibits axial compression upon proximal retraction of forming element 56. A metal ribbon comprising stainless steel, nitinol, or other known materials may be desired in certain embodiments, due to its ability to influence the plane of curvature of the device 40 when in the formed orientation.

The proximal extension 64 of the forming element 56 extends proximally throughout the length of the deployment catheter, to a control or free end which remains outside of the patient during the deployment procedure. Following placement of the device 40 in the coronary sinus, proximal traction on the proximal extension 64 will reconfigure the device 40 into the formed orientation within the coronary sinus, as will be discussed in connection with the method of the present invention. After a sufficient tension has been placed on the coronary sinus, the forming element 56 is preferably axially locked to the device 40, to resist distal movement of the forming element 56 through aperture 62. Any of a variety of locks 70 may be provided. Preferably, the lock 70 is provided on or near the proximal end 42, and, in particular, at or about the aperture 62. The lock may comprise any of a variety of structures, such as a suture knot, locking clamp or ring, an interference fit, ratchet and pall structures, an adhesive bond, or a compression fit, as will be apparent to those of skill in the art in view of the disclosure herein.

The lock 70 (on any of the embodiments herein) may be initially disengaged, so that the forming element 56 may be retracted or advanced freely through the aperture 62 while the physician adjusts the tension on the device 40. After the desired tension is achieved, the lock 70 is activated to engage the forming element in a manner which will depend upon the lock design. Alternatively, the lock 70 may be biased into an engaged configuration, such as with ratchet or cam structures, so that the forming element can only be retracted proximally. Preferably, however, the lock will allow the forming element to be released so that the physician can release tension in the device 40 in the event of momentary over tightening.

Figure 7:
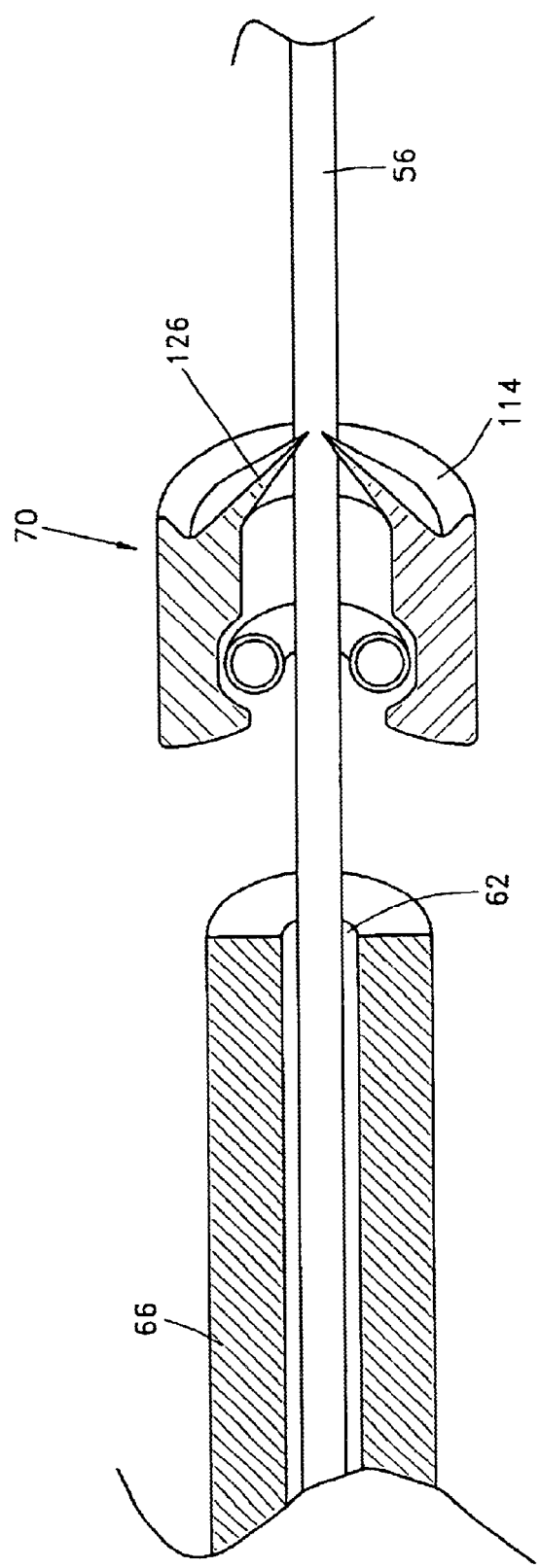
FIG. 7 is a schematic cross-sectional view of one embodiment of a locking device in accordance with the present invention.
Figure 8:
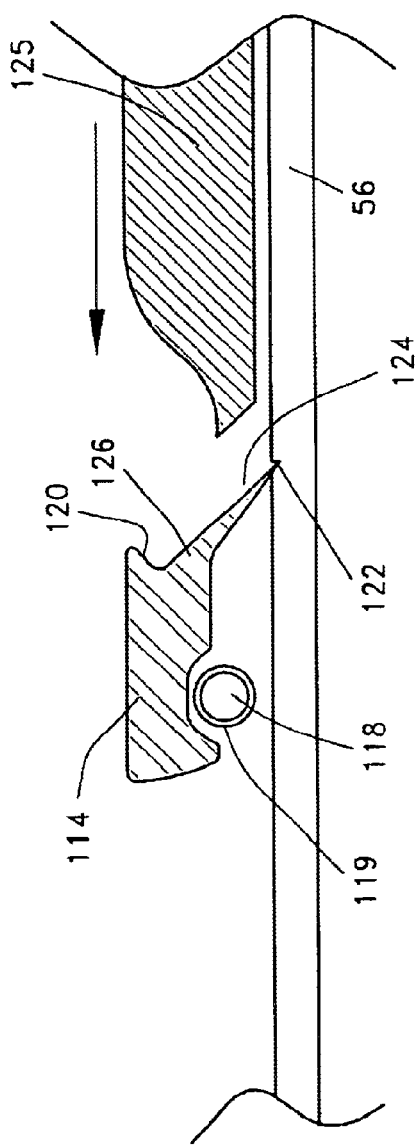
FIG. 8 is a fragmentary view of a portion of the lock illustrated in FIG. 7, with a locking tool.
Figure 9:
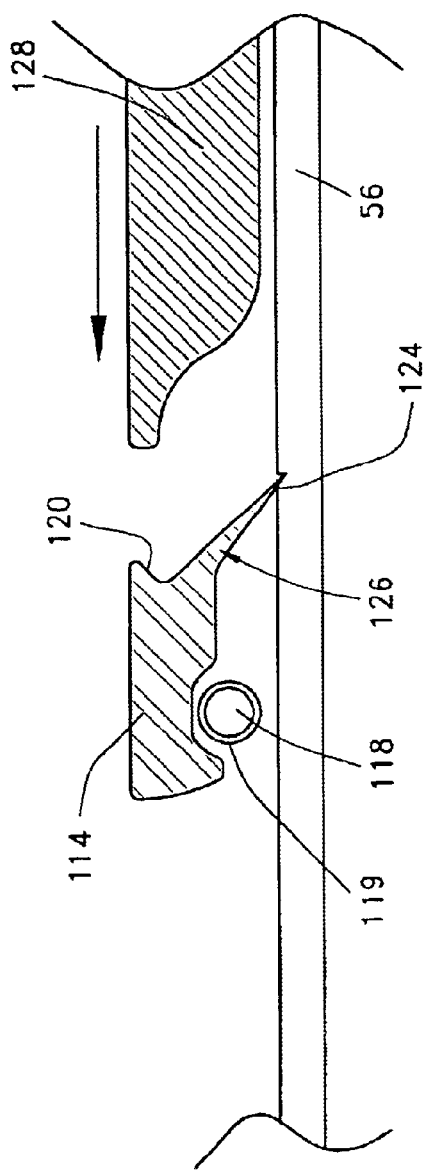
FIG. 9 is a fragmentary view as in FIG. 8, showing an unlocking tool.

Referring to FIGS. 7–9, there is disclosed one embodiment of a releasable lock 70 in accordance with the present invention. Although the lock 70 is illustrated as a discrete component of the system, it can alternatively be formed integrally with or attached to the proximal end of the body 66. The lock 70 comprises a body 114, which may be in the form of an annular collar with a central aperture for axial movement over the forming element 56. The body 114 is provided with one or two or three or more releasable locking elements 126 which ramp radially inwardly in the proximal direction.

Each locking element 126 is provided with at least one engagement surface 122 for engaging the forming element 56. The forming element 56 may be provided with any of a variety of friction enhancing surface textures or structures to enhance the locking function. Thus, a locking zone along the forming element may be provided with an etched surface or friction enhancing coating. Alternatively, structures such as a plurality of beads or teeth can be provided to permit an interference fit with the engagement surface 122.

The engagement surface 122 is movable between a first, disengaged configuration and a second, engaged configuration. This may be accomplished by pivoting the locking element 126 about a fulcrum 118. In the illustrated embodiment, fulcrum 118 is formed by an annular ring 119. Alternatively, the fulcrum 118 can be formed by plastic deformation of an integral structure, such as a living hinge formed by one or more annular grooves in the body 114.

The locking elements 126 may be biased in the locked direction, unlocked direction, or neutrally. Locking may be accomplished by pressing distally on a locking surface 124 such as with a locking tool 125 (FIG. 8) which applies distal pressure on the ramped locking element 126 at a point which is displaced radially inwardly from the fulcrum 118. Unlocking may be accomplished by distally advancing an unlocking tool 128 against a release surface 120 which is displaced radially outwardly from the fulcrum 118. In one embodiment, the locking tool 125 and unlocking tool 128 are conveniently formed from concentric tubular elements as will be apparent to those of skill in the art. The tubular elements or proximally extending control wires extend proximally to controls outside of the patient. Alternatively, any of a variety of ramped engagement surfaces and tools can be readily configured to accomplish the lock and/or release functions in view of the disclosure herein.

The length of the device 40 from proximal end 42 through the point of attachment 60 is generally within the range of from about 2 cm to about 10 cm, and, preferably within the range of from about 6 cm to about 8 cm. The shape of the device 40 is preferably designed to minimize trauma to the vascular intima, both during implantation and following placement. This may be accomplished by rounding all edges which may come into contact with the vessel wall. Thus, the cross-section through the mid portion 48 of the device, for example, may be elliptical, semicircular or otherwise rounded, or rectangular with rounded corners. In general, the maximum area of a cross-section of the device 40 will be no more than about 15 mm², and preferably no more than about 10 mm², for implantation within a human adult.

The device 40 may be manufactured in accordance with any of a variety of techniques, which will be apparent to those of skill in the art in view of the disclosure herein. For example, the body 66 may be formed by extrusion, injection molding, or other techniques. In one embodiment, the forming element 56 is secured at point of attachment 60 to an elongate flexible support 58 and coextruded within a polymeric body 66. Alternatively, the forming element 56 and support 58 subassembly may be positioned within a mold cavity, and injection molded to produce the final device 40. The body 66 may comprise any of a variety of biocompatible materials such as various densities of polyethylenes, nylon, polyethylene terephthalate, PEBAX, and others which will be apparent to those of skill in the art.

Alternatively, the forming element 56 and support 58 may be surrounded by a tubular jacket of ePTFE or Dacron fabric, or other material which is wrapped or stitched onto the forming element 56 to produce the final device 40. As a further alternative, the subassembly which includes the forming element 56 and, if present, support 58 may be positioned within a suitable length of tubing formed such as by extrusion. The tubing may be drawn down to a reduced diameter at the distal end 44. Additional post extrusion steps may be used to produce the desired cross-sectional configuration. Manufacturing techniques for the present invention will be apparent to those of skill in the art in view of the disclosure herein.

Any of a variety of additional features may be added to the device 40, depending upon the desired clinical performance. For example, the outside surface of the body 66 may be provided with any of a variety of coatings, such as Paralene, PTFE or others to improve lubricity; heparin or other antithrombogenic agents; elastomers such as silicone, neoprene, latex or others to soften the surface and reduce the risk of trauma to the vascular intima, and the like. Adhesion enhancing surfaces may be provided, such as ePTFE patches or jackets, to promote cellular ingrowth for long term anchoring. In addition, depending upon the deployment system design, the body 66 may be provided with a guidewire lumen extending axially therethrough, to allow the body 66 to be advanced distally over a guidewire during placement at the treatment site.

The device 40 may be implanted within the coronary sinus 22 either through direct surgical (e.g. thoracotomy with or without sternotomy) access, such as in combination with another surgical procedure, via port access, or remotely by way of a percutaneous or surgical cut down access to the venous system. Preferably, the device 40 is implanted in a transluminal procedure, such as by way of a percutaneous access at one of the internal jugular, subclavian, or femoral veins.

Figure 3:
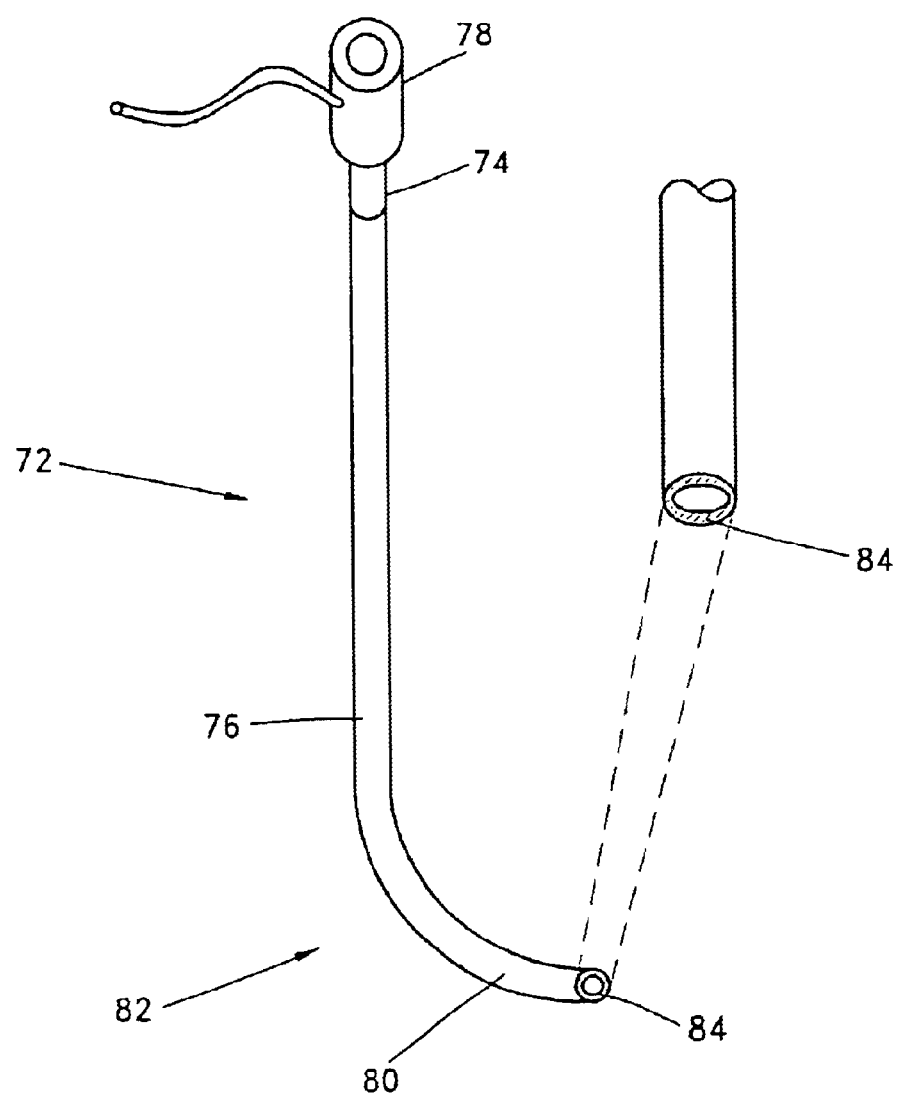
FIG. 3 is an overall view and cross-sectional view through a transvenous delivery sheath.
Figure 4:
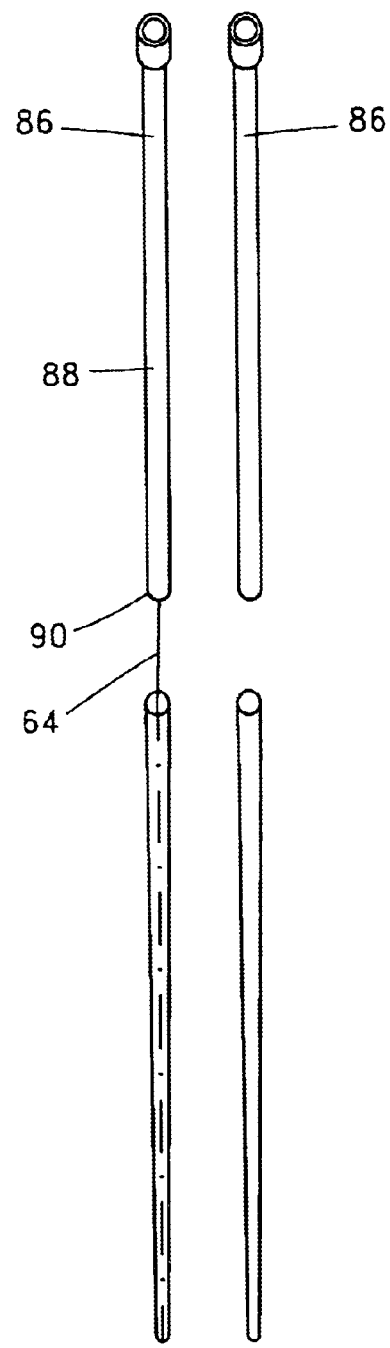
FIG. 4 is a schematic illustration of the delivery sheath and two different embodiments of the implant for extravascular remodeling, one with a forming element and one without.

Referring to FIG. 3, there is disclosed a deployment system 72 for deploying the device 40 of the present invention. The deployment system 72 comprises an introducer sheath or catheter 74 for percutaneous venous access procedures. In some circumstances, however, the system 72 includes a first introducer sheath 74 for simply gaining percutaneous access into the vasculature at a remote location from the heart, and a slideably engageable second introducer sheath or guiding catheter is deliverable through such a percutaneous introducer sheath. Introducer sheath 74 has an elongate flexible tubular body 76 extending from a proximal end 78 to a distal end 80. A preset curve 82 is provided near the distal end 80 of the tubular body 76, as is known in the cardiac access catheter arts. At least one lumen 84 extends through the tubular body 76. In one embodiment, the lumen 84 has a noncircular cross section, such as an ellipse having the major axis perpendicular to the plane of curvature of the introducer sheath 74.

Introducer sheaths are well known in the art, and may be manufactured such as by extrusion, with or without a braided reinforcement structure in the wall. The length and diameter of the introducer sheath 74 may vary considerably, depending upon the dimensions of the device 40 as well as the access point for percutaneous access into the vascular system. For a femoral vein access, for example, the introducer sheath may have a length within the range of from about 80 cm to about 120 cm. Preferably, the outside diameter of the introducer sheath 74 is no more than about 10 French (approximately 3.3 mm).

A pusher or dilator 86 as shown provides specific embodiments for a broader aspect that is a delivery member used in an overall assembly for delivering, i.e. advancing or pushing, the device prosthesis into the coronary sinus in a translumenal procedure, as is apparent to one of ordinary skill based upon the figures and accompanying disclosure herein. Delivery member or dilator 86 has an axial length of from about 10 cm to about 20 cm greater than the axial length of the introducer sheath 74. Dilator 86 has an outside diameter which is less than the inside diameter of the lumen 84, so that the dilator 86 may be freely axially advanced through the lumen 84. The dilator 86 is provided with a central lumen 88, for axially moveably receiving the proximal extension 64 of forming element 56.

When assembled for deployment of a device 40 within the coronary vasculature, a device 40 is positioned within a distal portion of the lumen 84. The dilator 86 is positioned proximal to the device 40 within the lumen 84, and the proximal extension 64 of forming element 56 extends proximally through central lumen 88 of dilator 86. During proximal movement of the introducer sheath 74 with respect to the dilator 86, a distal surface 90 on dilator 86 resists proximal movement of the device 40. Thus, the device 40 may be deployed from the distal end 80 of introducer sheath 74. In addition, proximal retraction of the proximal extension 64 while proximal movement of the device 40 is prevented by surface 90 causes the device 40 to advance from its deployment configuration to its implanted configuration.

Once the coronary sinus 22 has been cannulated by the introducer sheath 74, the dilator that is loaded over the forming element is advanced through the sheath 74. This is used to push the device 40 to the proper location with the distal tip 44 in the distal portion of the great cardiac vein 28. Using counter traction of the forming element and the dilator, the device is curved until the appropriate degree of annular remodeling has been achieved. A locking ring 70 on the forming element that is interposed between the dilator and the device prevents the forming element from slipping distally once the device 40 has been curved. A locking ring 70 that can be released by using a dilator with a different tip geometry may also be employed. After satisfactory deployment and deflection of the device 40, the forming element 56 is cut with a cutting tool (not illustrated) that is placed through the introducer sheath.

A second embodiment of the device does not contain an axially moveable forming element. Instead, a core of springy memory material such as nitinol or other NiTi alloy is pre-formed to have the required configuration. When the device is pushed out of the delivery catheter into the coronary venous system, the spring force within the core applies the requisite force to remodel the annulus. This embodiment does not require a tensioning element or a tool to disconnect it from the delivery system. However, the magnitude of force applied to the annulus cannot be adjusted.

A third embodiment is deployed as a loop through the coronary venous system, to form a left ventricular girdle 100. See FIGS. 5–6. The ventricular girdle 100 comprises an elongate flexible body 102 having a proximal end 104 and a distal end 106. A first control line 108 extends proximally from the proximal end 104, and a second control line 110 extends distally from distal end 106. The first and second control lines 108 and 110 may be different portions of the same wire, which extends continuously throughout the length of the body 102. The wire may be a single strand or multi strand component, a length of hypodermic needle tubing, a spring coil, or other structure known in the medical guidewire arts. Preferably, the first and second control lines have a diameter within the range of from about 0.009" to about 0.018", although larger diameters may also be used particularly for the first control line 108.

Figure 5:
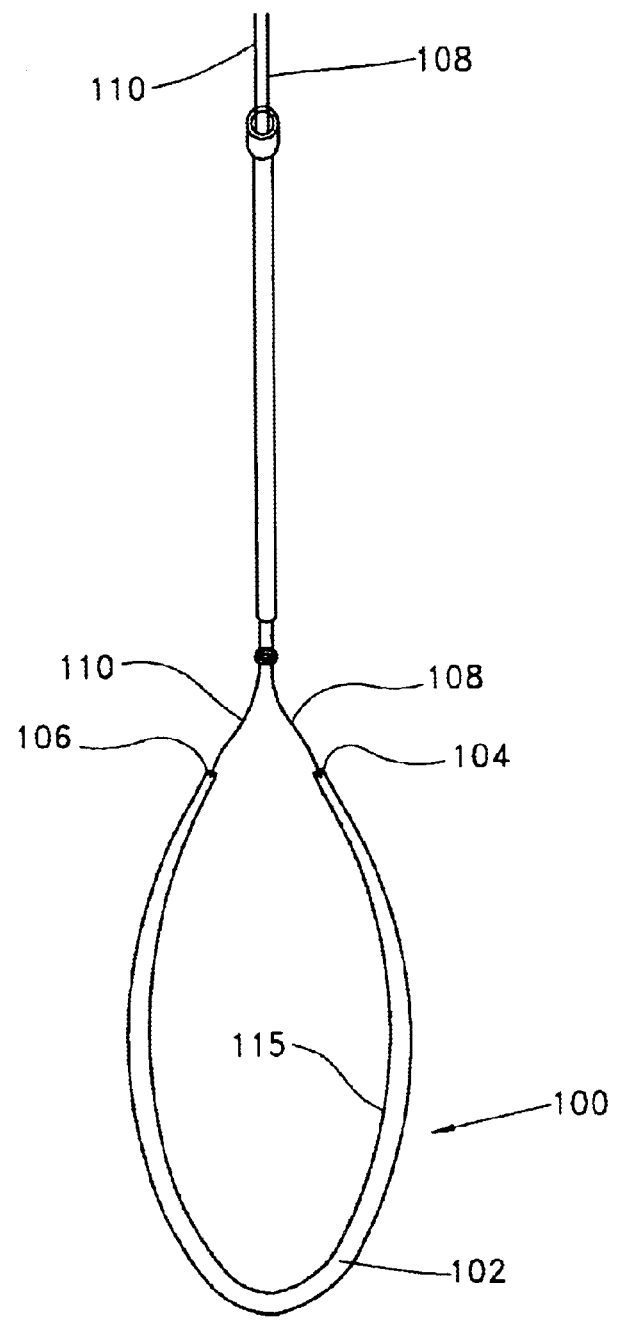
FIG. 5 is a schematic illustration of an alternative embodiment of the present invention positioned in an open-loop configuration through the delivery sheath.

The distal control line 110 is advanced through an introducer sheath into the great cardiac vein 28 and then through anastomotic connections 29 into the middle cardiac vein 30. Continued advancement results in the tip of the distal control line 110 emerging from the ostium 24 of the coronary sinus 22. The control line 110 is then harnessed with a snare and pulled retrogradely through the delivery catheter as illustrated in FIG. 5. The body 102 is then pulled into the coronary venous system. The body is preferably larger in diameter than the first and second control lines 108 and 110, and preferably elliptical or otherwise noncircular in cross section. This shape enlarges the transverse tissue contact surface area and reduces the risk of erosion when tension is applied to the loop. Both the proximal and distal ends of the loop are threaded through a locking clip 112. A dilator is used to push the clip 112 through the delivery catheter to the level of the coronary sinus ostium. Using counter traction on the dilator and the first and second control lines 108 and 110, the clip 112 is cinched on the loop until the requisite degree of tension is produced. Finally, the device is separated from the delivery system using a cutting tool to cut the first and second control lines 108 and 110, and possibly proximal and distal ends 104 and 106 to the extent they extend proximally from clip 112.

Figure 6:
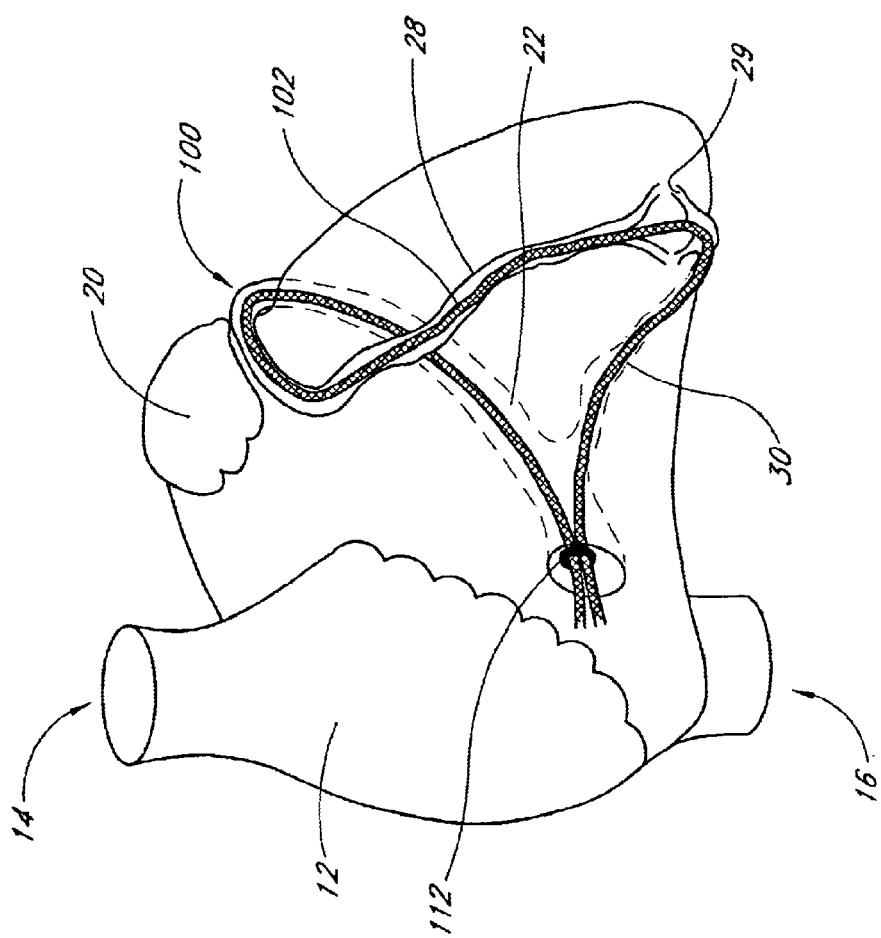
FIG. 6 is a schematic illustration of a heart, having an alternate embodiment of the mitral annuloplasty and cardiac reinforcement device of the present invention positioned within the coronary sinus and contiguous venous system.

The overall length of the embodiment illustrated in FIG. 5 should be sufficient that both of the first control line 108 and second control line 110 can extend outside of the patient, while the body 102 extends throughout the pathway of the ventricular girdle 100 as illustrated in FIG. 6. For a percutaneous femoral vein access, the overall length of the device is therefore preferably at least about 200 cm, and generally within the range of from about 220 cm to about 260 cm. The length of the body 102 from proximal end 104 to distal end 106 is preferably sufficient to form a closed loop as illustrated in FIG. 6. Although both heart size and the shape of the vascular pathway will vary from individual to individual, the length of the body 102 is generally within the range of from about 6 cm to about 12 cm. The body 102 may be injection molded, extruded as a tube, or coextruded over the wire which forms first and second control lines 108 and 110. Preferably, the body 102 either comprises or is coated with a material which is sufficiently compliant to minimize trauma to the vascular intima. Also, the transverse width of a tissue contacting surface 115 on body 102 is preferably sufficient to distribute compressive force to minimize the risks of localized pressure necrosis within the coronary veins.

FIGS. 10–13B variously show another particular device assembly 200 that includes various aspects that are believed to be readily adapted for use according to various of the embodiments of the present invention as introduced above.

Figure 10:
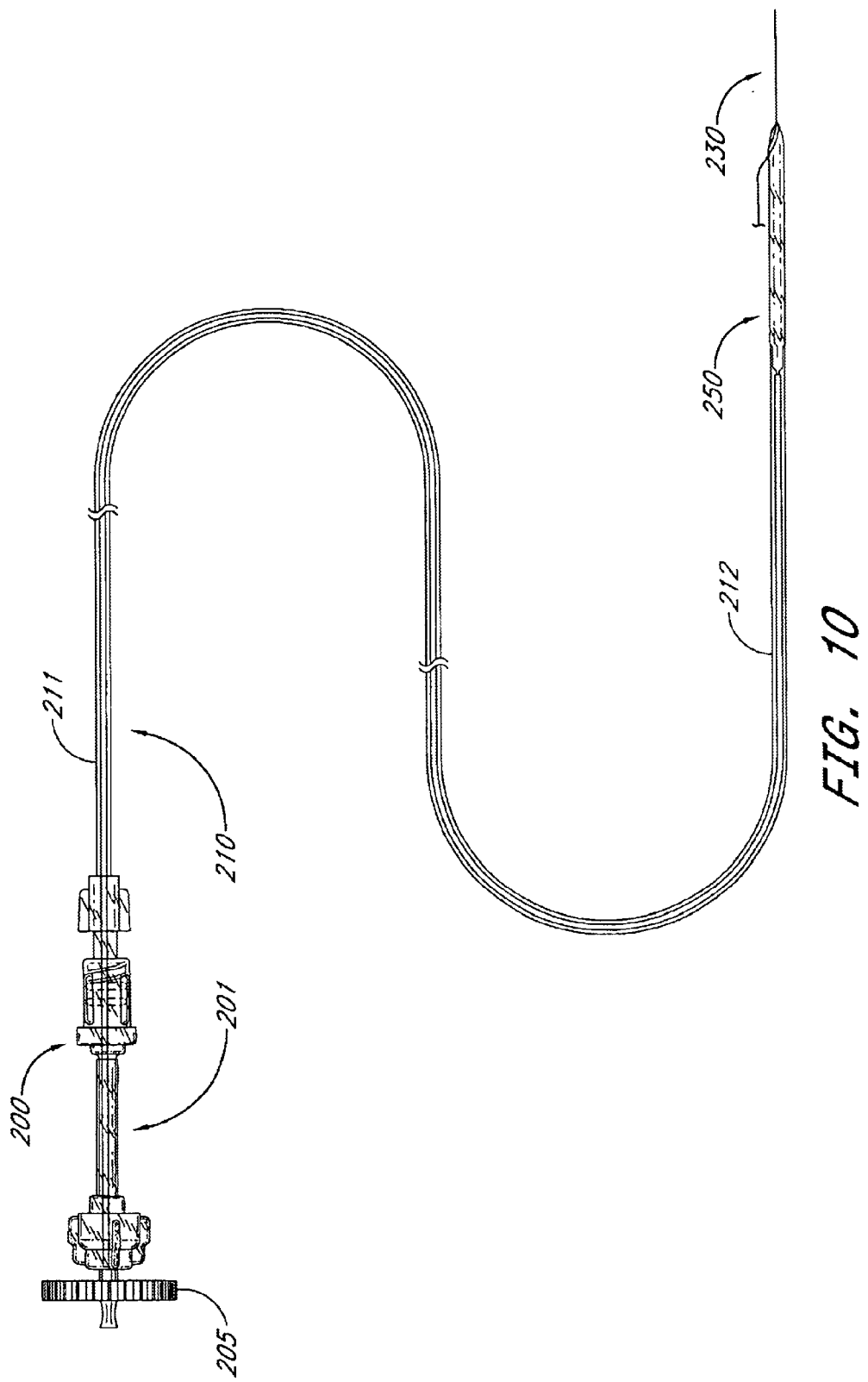
FIG. 10 is a perspective view of another device assembly according to the invention.

In general, FIG. 10 shows an overall view of assembly 200 that includes a delivery assembly 210 which is engaged to a prosthesis 250. According to similar overall delivery systems and methods elsewhere herein described, prosthesis 250 is adapted to be delivered in a first condition and shape into a vessel at least in part by manipulation of delivery assembly 210. Once in the desired region of the target vessel, prosthesis 250 is adapted to be adjusted to a second condition and shape within the vessel in order to influence an adjacent tissue structure. As also elsewhere herein described, a particularly beneficial mode of such operation places the prosthesis 250 within a coronary sinus for the purpose of influencing a mitral valve annulus, more specifically in order to influence the shape of the annulus in order to reduce mitral valve regurgitation.

FIGS. 11A–B show the proximal aspects of device assembly 200, and in particular various details for delivery assembly 210 that includes an outer member 215 that is generally tubular with an inner lumen 216 that is sized to house an inner member 225. Inner member 225 in the variation shown is generally tubular and is substantially free to rotate within lumen 216 by providing rotational force to inner member 225 proximally outside of the patient's body. According to the example shown, this rotational force is applied to inner member 225 via a thumbwheel 205 that is provided on proximal hub assembly 201 that is coupled to proximal end portion 211 of delivery assembly 210. Thumbwheel 205 is rotationally coupled to inner member 225 within hub assembly 201, which rotational coupling may be achieved according to a number of adaptions as would be apparent to one of ordinary skill.

Rotation of inner member 225 is transmitted into rotation of a rotational coupler 280 that is engaged within a proximal end portion 252 of prosthesis 250 as follows. Inner member 225 has an aperture 228 on its distal end portion that provides a female counterpart of a mated key interface between the inner member 225 and a male counterpart provided by a shaped proximal end 281 of a rotational coupler 280 that is also rotationally engaged within a proximal end portion 252 of prosthesis 250. The keyed fitting between inner member 225 and rotational coupler 280 allows for transmission of rotational forces to rotational coupler 280. In order to maintain releasable axial engagement of this keyed coupling, a flexible member such as a filament 240 is looped through an aperture 283 through proximal end 281 of rotational coupler 280 with both filament ends 242 and 244 extending proximally through inner member 225 to a location in proximal coupler. This filament 240 is generally held in sufficient tension to keep the distal keyed fitting engaged, though it is further contemplated that the mere presence of the filament may provide an interference against uncoupling if there is a sufficiently tight tolerance in the male/female interface of the keyed fitting.

Rotational coupler 280 is rotationally engaged within proximal end portion 251 of prosthesis 250 through proximal port or aperture 251 such that rotational coupler 280 is adapted to rotate within and relative to the prosthesis. This relative rotation is converted to force a deflection of prosthesis 250 into the desired shape of the second configuration in situ as follows.

According to one aspect of the rotational coupling, the prosthesis 250 is preferably held to resist rotation while rotational coupler 280 is rotated within the prosthesis 250. This may be achieved simply by frictional forces of surrounding tissue as prosthesis 250 is delivered into the desired vessel such as the coronary sinus. According to another example, this may be achieved by providing a releasable interface 218 such as a friction fit between outer member 215 and proximal end portion 252 of prosthesis 250, wherein the frictional engagement of outer member 215 and prosthesis 250 are held in a relatively fixed position while inner member 225 and rotational coupler 280 are rotated. This embodiment is shown in FIG. 11A. In addition or in the alternative to the friction fit interface, a keyed interface may be employed as shown in FIGS. 12A–B. According to this mode, a shaped proximal fitting 253 on the proximal end 252 of prosthesis 250 is adapted to mate as a male counterpart into a shaped aperture or fitting on the distal end 212 of outer member 215. This keyed interface allows for rotational coupling between the members in a similar manner as just described for the inner member 225 and rotational coupler 280, and may allow for a more releasable coupling with reduced friction upon axial detachment of the members.

Figure 13A:
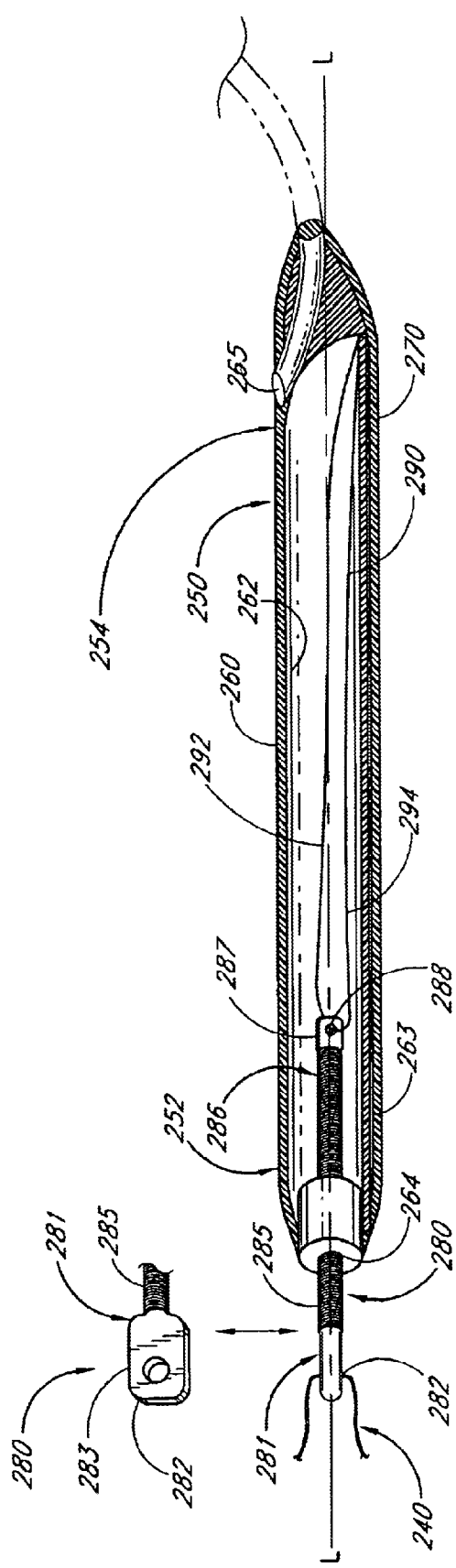
FIG. 13A shows a partially cross-sectioned exploded side view of a distal prosthetic implant region of a device assembly similar to that shown in FIG. 10, and shows the distal prosthetic implant region in a first configuration during a first mode of use.
Figure 13B:
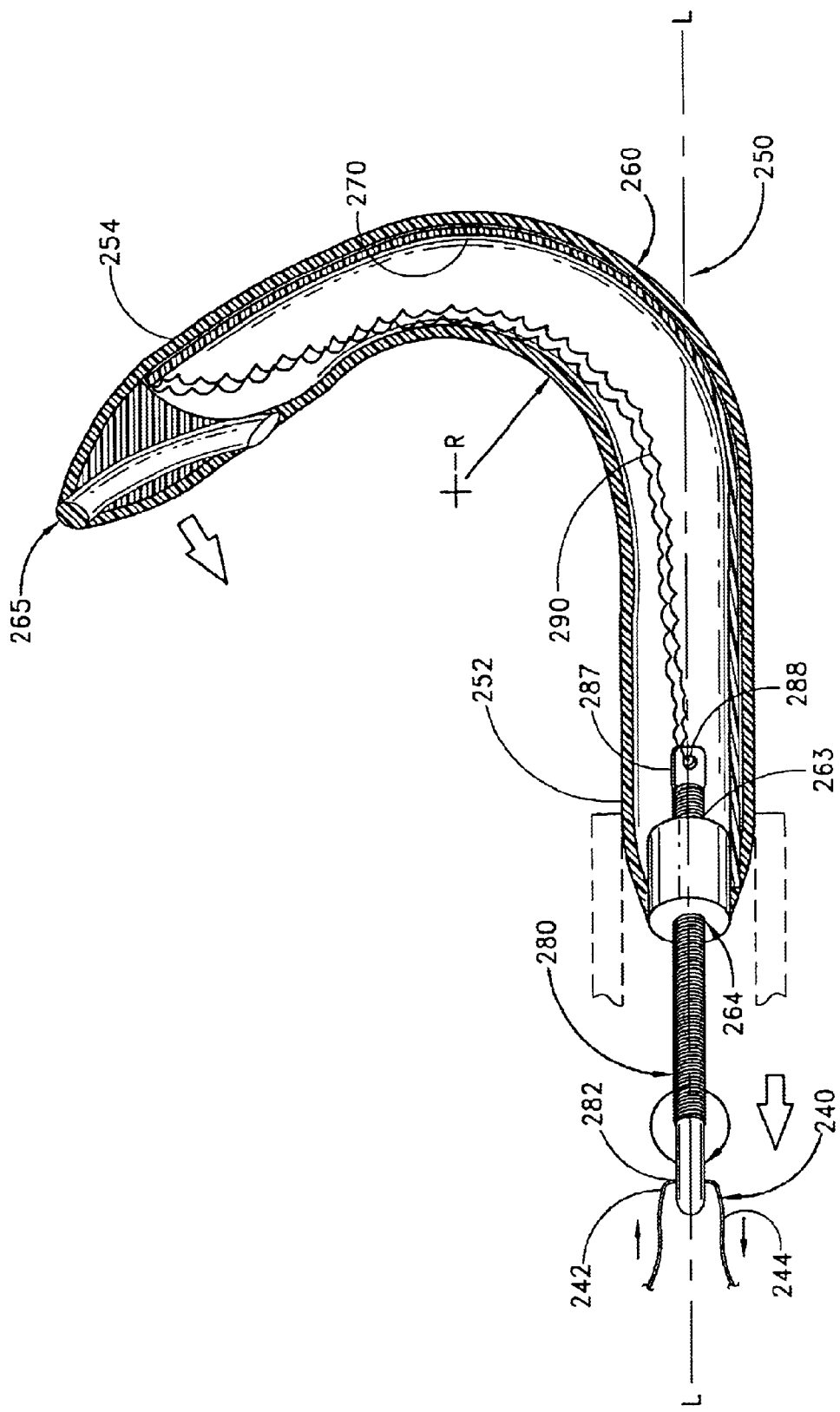
FIG. 13B shows a similar view as that shown in FIG. 13A, and shows the distal prosthetic implant region in a second configuration during a second mode of use.

According to another aspect, the rotational forces from rotational coupler may be converted to deflection forces on the prosthesis 250 according to one example as illustrated in the specific illustrative embodiment of FIGS. 10–13B, and in particular detail in FIGS. 13A–B. Prosthesis 250 includes a generally tubular wall or body 260 that has an inner lumen 262 and extends from the proximal end portion 252 to the distal end portion 254 of prosthesis 250. Secured along proximal end portion 252 is a nut fitting 263 that has a grooved inner bore 264 which communicates with inner lumen 262. Further to this specific embodiment, rotational coupler 280 is a screw member with outer groove or grooves 285 engaged within the mating grooved inner surface (not shown) of a bore lumen 264 such that a distal end of screw member 285 extends distally within lumen 262 and terminates at a second key fitting 287 similar to the shaped proximal end portion 282 and also having an aperture 288. Similar to the proximal end of rotational coupler 280, another flexible member or filament 290 is looped through aperture 288 such that two arms 292,294 extend distally therefrom to an attachment point along distal end portion 254 of prosthesis 250. Because nut fitting 263 is fixed in relation to outer tubular body 260, and because that tubular body is held relatively fixed position as provided above, rotation of rotational coupler 280 moves coupler 280 proximally relative to body 260. This proximal axial translation of rotational coupler pulls tension on filament 290, which pulls tension on the body 260 due to the distal attachment. This tension on outer body 260 forces a deflection of that body. Therefore, rotational forces are translated into tensile forces which are translated into radial deflection forces relative to the longitudinal axis L of the device.

The forced deflection just described may be controlled in a particular plane by providing a composite structure within prosthesis 250 that is engineered to respond, i.e. yield, to these forces in a prescribed way. In the specific desirable embodiment shown, a relatively rigid spine member 270 is provided within lumen 262 of outer tubular body 260. This spine member 270 is more rigid and more resistant to axial forces than the material of outer tubular body 260 alone, and therefore providing spine member 270 along only one radial aspect of the prosthesis 250 creates a bias on the device to deflect away from that spine toward a more compressive region of the device. Such composite design may further include a laminant structure, imbedded wire reinforced wall structure, or may be achieved by engineering material variations in the device, such as for example by thinning, thickening, hardening, or softening the material at one location along the outer tubular body 260 relative to another region to force deflection at a desired location.

As may be achieved by other controllable embodiments elsewhere herein described, deflection according to the present embodiment may be adjusted according to a healthcare provider's desires, and is adjustable in either direction—by either tightening the radius of curvature R or opening it. According to this specific embodiment however, the adjustability of and choice between tightening and loosening of the deflection depends upon the direction and extent of rotation placed upon the rotational force transmission system.

In any event, once the desired deflection is achieved and desired therapeutic results are observed, the prosthesis 250 may be detached from the delivery assembly 210 by severing the torque or rotational force transmission system at the keyed fitting between the inner member 225 and the rotational coupler 280. This is accomplished by first releasing at least one arm 242,244 of the proximal filament 240 while withdrawing the other arm, thereby threading the filament 240 through aperture 283 (as shown in bold arrows in FIG. 13B) until it is unthreaded completely from the aperture 283. This allows inner member 225 to be withdrawn proximally from rotational coupler 280 to detach therefrom and thereby implant prosthesis 250. Alternatively, as with other adjustable deflection systems herein described, the prosthesis may be held in its therapeutic condition for a temporary period of time (which may nevertheless be prolonged during a hospital stay), during which time mitral valve regurgitation may be minimized, such as for example for the purpose of bridging the patient in a temporarily improved condition until other treatments may be performed, e.g. annuloplasty, valve surgery, heart transplant, etc. In this alternative temporary setting, at the appropriate time the deflected, contracted prosthesis may be adjusted back open from its cinched position around the valve, and then withdrawn without implantation by withdrawing the entire system, delivery assembly still engaged to the prosthesis. Moreover, it is further contemplated that such a temporary prosthesis may be modified to remove the detachment mechanisms herein described, which may provide for a simpler and lower cost device.

Device assembly 200 is also shown in various of the FIGS. 10–13B to include a distal guidewire tracking member with a guidewire lumen 265 which is adapted to slideably engage a guidewire 230 in order to be placed in a percutaneous translumenal procedure into the desired vessel location, such as within the coronary sinus. The particular guidewire lumen shown is integral within the distal aspects of prosthesis 250 as a "rapid exchange" or "monorail" design that allows for relatively independent movement of the guidewire and catheter in vivo. Moreover, this design removes the need for the guidewire to ride coaxial through the entire device assembly 200, as would be the case for example in an "over the wire" type system. The type shown beneficially allows for detachable engagement of prosthesis 250, which is preferably achieved after withdrawing the guidewire from the distal lumen 265.

In each of the foregoing implantation methods, the physician preferably monitors the degree of regurgitation during the step of tightening the implant. Although any reduction in mitral regurgitation may be desirable, regurgitation is preferably reduced to something less than moderate (less than 2+). In any event, at least a one grade reduction is preferably achieved. On the other hand, reconfiguration of the implant should not be accomplished to an extent sufficient to produce mitral stenosis, or any flow limitation of hemodynamic significance.

Thus, the method of implantation preferably further comprises the steps of monitoring the degree of mitral regurgitation during the implantation and/or reconfiguration steps. The degree of mitral regurgitation may be monitored such as by transesophageal echo cardiography, surface echo cardiography, intracardiac echo cardiography, fluoroscopy using radiocontrast in the left ventricle (LVgram), or left atrial or pulmonary capillary wedge pressure tracings, as are understood in the art, during the incremental restriction of the mitral annulus and/or left ventricle step. Once a sufficient reduction in regurgitation has been achieved for a particular patient in the physician's judgement, the device is locked and the proximal extension of the forming element is severed from the device and removed from the patient.

The method may additionally comprise the step of measuring the coronary sinus and/or other coronary vein, and selecting an appropriately sized implant from an array of implants of varying sizes. Such parameters may include diameter, length, or radius of curvature of the arc of the sinus. The appropriately sized implant is thereafter positioned within the target vein. The implant is thus preferably provided in a graduated array of sizes, so that the optimal size can be selected for each patient. The size of the coronary sinus or other vein can be measured using any of a variety of techniques, such as echo cardiogram, MRI, CT scan, or angiography as is understood in the art. Moreover, as is apparent to one of ordinary skill, measuring a parameter of the coronary sinus generally provides indicia of certain parameters of the mitral valve and its annulus, such as for example mitral valve diameter, in which case either the coronary sinus parameter or the mitral valve parameter may provide the requisite information for choosing an appropriately dimensioned device from the kit. It follows that such mitral valve parameters may further be measured directly, such as by various of the methods just described, in order to generate the values used for choosing the appropriate device. Once a parameter for an anatomical feature is measured as herein described, its value is generally estimated according to the accuracy of the respective measuring tool—it is contemplated that persons without specialized medical skills or training can choose the appropriate medical device from the kit once armed with this estimated value. For example, packaging for each device of the kit may indicate the respective dimensions that are unique to that device with respect to other devices of the kit, and the estimated value of the measured anatomical parameter may simply be compared.

It is contemplated and apparent that various of the embodiments herein described are adapted to accomplish device manipulation within the coronary sinus for mitral annulus reduction without substantially altering the length of the device within the sinus. This may provide a benefit by increasing the useful purchase of the device along the coronary sinus and circumferentially around the mitral annulus as the sinus length and/or annulus diameter may be reduced during remodeling from the radial deflection of the prosthetic device. This may also mean that the dimension of the device in a kit of devices may not directly correspond to the estimated value of the anatomical parameter that is measured. For example, the compared value of the measured device parameter may be shorter than an estimated coronary sinus length due to a possible shortening of the sinus during device treatment. Or, the anatomical parameter may be estimated from an initial value based upon an anticipated or desired final result from treatment and such procedurally related value be used for choosing the appropriate device (e.g. comparing an estimated final length of the sinus or mitral valve diameter with a known dimension of the device in the remodeling configuration when used in situ).

As a further aspect to the present invention, the implant is preferably combined with an appropriate drug therapy for treating congestive heart failure. Residual regurgitation and other hemodynamic functions are preferably measured following implantation of the implant of the present invention. Heart medications are preferably adjusted to take into account the reduction in regurgitation and/or reduction in left ventricle volume in formulating an ongoing drug therapy for the patient.

Still further, the aspect of the present invention that allows for temporary use in the sinus for mitral valve remodeling as a bridging regime in combination with other permanent treatments such as more conventional annuloplasty or valve replacement via surgery. Such combined systems of devices and respective methods of use, which may further be combined with the pharmaceutical drug regimes, provide an overall treatment regime that provides a highly beneficial result for management of patients with harmful mitral valve regurgitation.

In accordance with further aspect of the present invention, there is provided a method of constricting the left ventricle. Left ventricular constriction may be desirable in patients without mitral regurgitation. One implementation of this method comprises implanting the ventricular girdle 100 as illustrated, for example, in FIGS. 5 through 6 and previously discussed herein.

Any of the embodiments disclosed herein may additionally be provided with one or more externally facing electrically conductive axially extending strips or annular bands, to enable the device 40 to function additionally as a cardiac pacing or other cardiac electrode. The electrically conductive band or bands are placed in electrical communication with a pacing source or diagnostic instrument by way of one or more electrical conductors extending away from the device 40. The conductors may be electrically connected to any of a wide variety of electronic cardiac rhythm management devices, which are well known in the art.

Although the present invention has been described in terms of certain preferred embodiments, it may be incorporated into other embodiments or performed through other steps by persons of skill in the art in view of the disclosure herein. The scope of the invention is therefore not intended to be limited by the specific embodiments disclosed herein, but is intended to be defined by the full scope of the following claims.

What is claimed is:

1. A method of performing transluminal mitral annuloplasty, comprising the steps of:
   providing a catheter, having a prosthesis thereon, the catheter having a rotatable member extending axially therethrough and releasably engaged with a rotatable component of the prosthesis;
   inserting the catheter into the venous system;
   transluminally advancing the prosthesis into the coronary sinus;
   rotating a component of the prosthesis to cause the prosthesis to exert a compressive force on adjacent atrial musculature;
   releasing the rotatable member from the prosthesis; and
   removing the rotatable member from the patient.

2. The method of claim 1, further comprising the step of percutaneously accessing the venous system prior to the transluminally advancing step.

3. The method of claim 2, wherein the accessing step is accomplished by accessing one of the veins selected from the group consisting of internal jugular, subclavian and femoral veins.

4. The method of claim 1, further comprising the steps of first measuring the coronary sinus and then selecting an appropriately sized prosthesis prior to the inserting step.

5. The method of claim 1, further comprising the step of measuring hemodynamic function following the rotating step.

6. The method of claim 5, further comprising the steps of determining an ongoing drug therapy taking into account the post implantation hemodynamic function.

7. The method of claim 1, wherein the rotating a component step causes the prosthesis to bend into an arcuate configuration.

8. The method of claim 7, further comprising the step of locking the prosthesis in the arcuate configuration.

9. The method of claim 8, wherein the locking step comprises engaging a first threaded surface with a second threaded surface.

10. The method of claim 8, wherein the locking step comprises providing an interference fit.

11. The method of claim 8, wherein the locking step comprises providing an adhesive bond.

12. The method of claim 8, wherein the locking step comprises providing a knot.

13. The method of claim 8, wherein the locking step comprises providing a compression fit.

14. The method of claim 1, further comprising the step of deploying the prosthesis in the coronary sinus.

15. The method of claim 14, further comprising the step of removing the catheter from the venous system.

16. The method of claim 1, additionally comprising the step of monitoring hemodynamic function to assess mitral valve regurgitation.

17. The method of claim 16, wherein the monitoring step comprises monitoring hemodynamic function prior to the rotating step.

18. The method of claim 16, wherein the monitoring step comprises monitoring hemodynamic function during the rotating step.

19. The method of claim 16, wherein the monitoring step comprises monitoring hemodynamic function following the rotating step.

20. The method of claim 16, wherein the rotating step results in axially moving a forming element with respect to the prosthesis, to bend the prosthesis.

21. The method of claim 16, wherein the transluminally advancing step is accomplished using a catheter.

22. The method of claim 16, further comprising the steps of first measuring the coronary sinus and then selecting an appropriately sized prosthesis prior to the inserting step.

23. The method of claim 16, wherein the step of monitoring hemodynamic function is accomplished using transesophageal echo cardiography.

24. The method of claim 16, wherein the step of monitoring hemodynamic function is accomplished using surface echo cardiographic imaging.

25. The method of claim 16, wherein the step of monitoring hemodynamic function is accomplished using intracardiac echo cardiographic imaging.

26. The method of claim 16, wherein the step of monitoring hemodynamic function is accomplished using fluoroscopy with radiocontrast media.

27. The method of claim 16, wherein the step of monitoring hemodynamic function is accomplished using left atrial or pulmonary capillary wedge pressure measurements.

28. The method of claim 16, further comprising the step of tightening the prosthesis to reduce regurgitation.

29. The method of claim 28, wherein the tightening step is performed to achieve at least a one grade reduction in regurgitation.

30. A method of performing transluminal mitral annuloplasty, comprising the steps of:
provinding a catheter, having a rotatable core extending therethrough and a prosthesis removably engaged with the core;
inserting the catheter into the venous system;
transluminally advancing the prosthesis into the coronary sinus;
rotating the core to rotate a first component of the prosthesis with respect to a second component of the prosthesis; and
releasing the prosthesis from the catheter, such that the rotatable core is disengaged from the prosthesis and the prosthesis exerts a force on the wall of the coronary sinus.

31. The method of claim 30, further comprising the step of percutaneously accessing the venous system prior to the transluminally advancing step.

32. The method of claim 31, wherein the accessing step is accomplished by accessing one of the veins selected from the group consisting of internal jugular, subclavian and femoral veins.

33. The method of claim 30, further comprising the steps of first measuring the coronary sinus and then selecting an appropriately sized prosthesis prior to the inserting step.

34. The method of claim 30, further comprising the step of measuring hemodynamic function following the rotating step.

35. The method of claim 34, further comprising the step of determining an ongoing drug therapy taking into account post implantation hemodynamic function.

36. The method of claim 30, further comprising the step of changing the shape of the prosthesis from an implantation configuration to a remodeling configuration in response to the rotating step.

37. The method of claim 36, wherein the prosthesis is reversibly movable between an implantation configuration for transluminal implantation and a remodeling configuration for exerting a force against a vessel wall.

38. The method of claim 36, wherein the prosthesis defines an arc when in the remodeling configuration.

39. The method of claim 36, wherein the changing the shape step comprises forming an arc which is concave in the direction of the mitral valve.

40. The method of claim 38, wherein a best fit constant radius curve corresponding to the arc has a radius within the range of from about 10 mm to about 20 mm.

41. The method of claim 30, further comprising the step of retaining the body in a remodeling configuration following the rotating step.

42. The method of claim 41, wherein the retaining step comprises engaging a lock on the prosthesis.

43. The method of claim 42, wherein the lock comprises an interference fit.

44. The method of claim 42, wherein the lock comprises a ratchet.

45. The method of claim 42 wherein the lock comprises an engagement surface, which is movable between a first, disengaged configuration and a second, engaged configuration.

46. The method of claim 42, wherein the lock is biased in a locked direction.

47. The method of claim 42, wherein the lock is biased in an unlocked direction.

48. The method of claim 30, further comprising a coating on the prosthesis.

49. The method of claim 30, further comprising the step of deploying an anchor for retaining the prosthesis at a deployment site within a vessel.

50. The method of claim 49, wherein the anchor comprises a distal extension of the implant.

51. The method of claim 49, wherein the anchor comprises a friction enhancing surface structure for engaging the wall of the vessel.

52. The method of claim 49, wherein the deploying an anchor step comprises deploying at least one barb for piercing the wall of the vessel.

53. The method of claim 30, wherein the prosthesis has an axial length of no more than about 10 cm.

54. The method of claim 30, wherein the cross sectional area through the implant is no more than about 10 mm$^2$.

55. The method of claim 30, additionally comprising the step of monitoring hemodynamic function to assess mitral valve regurgitation.

56. The method of claim 55, wherein the monitoring step comprises monitoring hemodynamic function prior to the rotating step.

57. The method of claim 55, wherein the monitoring step comprises monitoring hemodynamic function during the rotating step.

58. The method of claim 55, wherein the monitoring step comprises monitoring hemodynamic function following the rotating step.

59. The method of claim 55, wherein the step of monitoring hemodynamic function is accomplished using transesophageal echo cardiography.

60. The method of claim 55, wherein the step of monitoring hemodynamic function is accomplished using surface echo cardiographic imaging.

61. The method of claim 55, wherein the step of monitoring hemodynamic function is accomplished using intracardiac echo cardiographic imaging.

62. The method of claim 55, wherein the step of monitoring hemodynamic function is accomplished using fluoroscopy with radiocontrast media.

63. The method of claim 55, wherein the step of monitoring hemodynamic function is accomplished using left atrial or pulmonary capillary wedge pressure measurements.

64. The method of claim 55, further comprising the step of determining an ongoing drug therapy taking into account post implantation hemodynamic function.

65. The method of claim 30, further comprising the step of locking the prosthesis to retain a compressive force on the annulus following the manipulating step.

* * * * *